United States Patent
Chu et al.

(10) Patent No.: US 9,949,813 B2
(45) Date of Patent: Apr. 24, 2018

(54) INCONTINENCE IMPLANT ASSEMBLY

(71) Applicant: Boston Scientific Scimed, Inc., Maple Grove, MN (US)

(72) Inventors: Michael S. H. Chu, Brookline, MA (US); Kenneth M. Flynn, Woburn, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 487 days.

(21) Appl. No.: 14/199,614

(22) Filed: Mar. 6, 2014

(65) Prior Publication Data

US 2014/0257024 A1    Sep. 11, 2014

Related U.S. Application Data

(60) Provisional application No. 61/775,075, filed on Mar. 8, 2013.

(51) Int. Cl.
*A61F 2/00* (2006.01)

(52) U.S. Cl.
CPC .................. *A61F 2/0045* (2013.01)

(58) Field of Classification Search
CPC ..................................... A61F 2/0045
USPC ..................................... 600/29, 30
See application file for complete search history.

(56) References Cited

U.S. PATENT DOCUMENTS

| | | | | |
|---|---|---|---|---|
| 2002/0151910 | A1* | 10/2002 | Gellman | A61B 17/00234 606/139 |
| 2003/0004395 | A1* | 1/2003 | Therin | A61F 2/0045 600/37 |
| 2004/0039453 | A1* | 2/2004 | Anderson | A61B 17/0401 623/23.72 |
| 2004/0225181 | A1* | 11/2004 | Chu | A61B 17/06109 600/37 |
| 2005/0131391 | A1* | 6/2005 | Chu | A61B 17/00234 606/1 |
| 2005/0131393 | A1* | 6/2005 | Chu | A61B 17/00234 606/1 |
| 2005/0177022 | A1* | 8/2005 | Chu | A61B 17/0469 600/30 |
| 2005/0277807 | A1* | 12/2005 | MacLean | A61B 17/06066 600/30 |
| 2006/0089525 | A1* | 4/2006 | Mamo | A61B 17/0401 600/37 |
| 2006/0260618 | A1* | 11/2006 | Hodroff | A61B 17/06066 128/830 |
| 2007/0123915 | A1* | 5/2007 | Kammerer | A61F 2/0045 606/151 |
| 2008/0161837 | A1* | 7/2008 | Toso | A61F 2/0045 606/151 |
| 2008/0177132 | A1* | 7/2008 | Alinsod | A61F 2/0045 600/37 |
| 2008/0207989 | A1* | 8/2008 | Kaleta | A61B 17/06109 600/37 |

(Continued)

*Primary Examiner* — Navin Natnithithadha
*Assistant Examiner* — Sunita Reddy
(74) *Attorney, Agent, or Firm* — Brake Hughes Bellermann LLP

(57) ABSTRACT

According to an example embodiment, an implant assembly may include a first handle, a first elongated member defining a first lumen, and a tissue support member extending through the first lumen of the first elongated member, the tissue support member including a first end and a second end, the first end being attached to the first handle.

16 Claims, 9 Drawing Sheets

(56) References Cited

U.S. PATENT DOCUMENTS

| | | | |
|---|---|---|---|
| 2009/0171140 A1* | 7/2009 | Chu | A61B 17/0482 600/37 |
| 2009/0171143 A1* | 7/2009 | Chu | A61B 17/0401 600/37 |
| 2010/0191038 A1* | 7/2010 | Kubalak | A61F 2/0045 600/30 |
| 2011/0124954 A1* | 5/2011 | Ogdahl | A61F 2/0045 600/30 |

* cited by examiner

INCONTINENCE IMPLANT ASSEMBLY

CROSS REFERENCE TO RELATED APPLICATION

This application is a Nonprovisional of, and claims priority to, U.S. Patent Application No. 61/775,075, filed on Mar. 8, 2013, entitled "INCONTINENCE IMPLANT ASSEMBLY", which is incorporated by reference herein in its entirety.

TECHNICAL FIELD

This description relates to slings or implants for treating urinary incontinence.

BACKGROUND

For patients with urinary incontinence, a medical practitioner may implant a sling into the patient to hold the patient's urethra in place or otherwise provide support to the urethra. In some cases, the practitioner may have difficulty in positioning the sling and applying the desired tension to the sling.

SUMMARY

According to one general aspect, an implant assembly may include a first handle, a first elongated member defining a first lumen, and an incontinence sling extending through the first lumen of the first elongated member, the incontinence sling including a first end and a second end, the first end being attached to the first handle.

According to another general aspect, a method of assembling an implant for incontinence repair may include inserting an end of an incontinence sling into a first end of a handle, cutting at least a first aperture and a second aperture into an elongated member, the elongated member defining a lumen, each of the first and second apertures extending from outside the elongated member into the lumen, threading the handle and the incontinence sling through the first aperture from outside the elongated member into the lumen, threading the handle and incontinence sling through the second aperture from inside the lumen to outside the elongated member, aligning a second end of the handle with an end of the elongated member, the second end of the handle being opposite from the first end of the handle, and attaching a dilator to the second end of the handle.

According to another general aspect, a method of inserting a sling into a patient to treat incontinence may include inserting the sling into the patient through a vaginal incision in the patient, at least one end of the sling being attached to a handle, a portion of the sling extending through a lumen of an elongated member, securing the sling inside the patient with a portion of the elongated member extending out of the vaginal incision into the patient's vagina, and cutting off at least a portion of at least one of the handle and the elongated member from the sling after securing the sling inside the patient.

The details of one or more implementations are set forth in the accompanying drawings and the description below. Other features will be apparent from the description and drawings, and from the claims.

DETAILED DESCRIPTION

Figure 1:
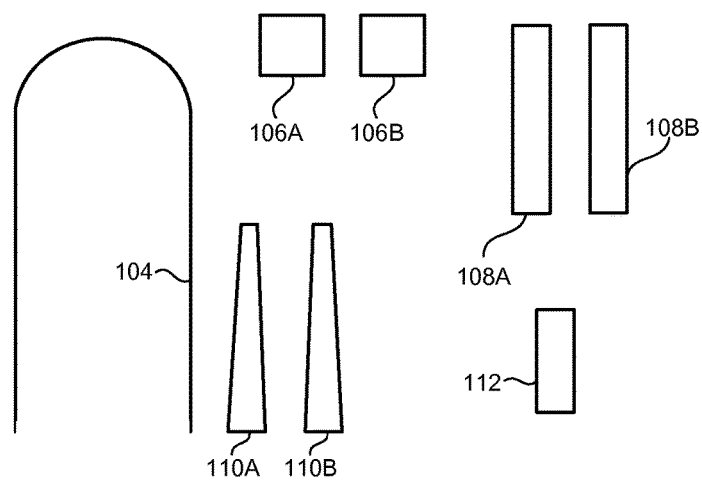
FIG. 1 is a schematic illustration of components of an implant assembly for treating incontinence.

FIG. 1 is a diagram of components of a sling assembly and/or implant. In some embodiments, the sling assembly is configured to be inserted or implanted within a body of a patient and configured to provide support to a portion of the body of the patient. For example, in some embodiments, the sling assembly or implant is configured to be disposed adjacent a urethra of a patient and provide support to the urethra. In some embodiments, the sling assembly may be used for treating incontinence, such as urinary incontinence. The components may be sold individually, collectively, or in any combination of some or all of the components. In an example implementation, the components may be assembled and then sold. The components may be assembled into the forms shown in the below embodiments, and then sold in the assembled form shown in the below embodiments. The components are not drawn to scale in FIG. 1. A manufacturer may assemble the implant assembly using the components shown in FIG. 1. The manufacturer may provide the assembled implant assembly to a medical practitioner, who may then use the implant assembly to perform incontinence repair on a patient.

One of the components of the implant assembly may be a sling 104. The sling 104 may include an incontinence sling. The sling 104 may also be referred to an implant, a support member, or a mesh. The sling 104 may be made of a flexible material, including a mesh material, such as polypropylene mesh. The sling 104 may include tangs on one or both ends. The tangs may be configured to bind to or grasp the patient's tissue, preventing, or helping to prevent, the sling 104 from moving within the patient and securing the sling 104 inside the patient.

The implant or sling 104 can be made of, or can include, a synthetic material. In some embodiments, the synthetic material can be, or can include, for example, as a polymeric mesh body, a polymeric planar body without mesh cells and structures, and/or so forth. In some embodiments, the synthetic material can include polypropylene, polyester, polyethylene, nylon, polyvinyl chloride (PVC), polystyrene, poly (styrene-isobutylene-styrene (SIBS), and/or so forth. In some embodiments, a mesh body of the synthetic material can be made of a non-woven polymeric material. In some embodiments, the synthetic material can include a Polyform® Synthetic Mesh developed by the Boston Scientific Corporation. The Polyform® Synthetic Mesh can be made from uncoated monofilament macro-porous polypropylene. In some embodiments, the mesh can be formed of or include a woven structure, a non-woven structure, a knitted structure, or a braided structure. In some embodiments, the mesh is tied, twisted, or layered. In some embodiments, the mesh is formed of single or multifilaments. In some embodiments, the mesh is formed of or includes a sheet or a plurality of sheets and may or may not include pores or openings. In some embodiments, the sling or mesh can have a specified weight. In some embodiments, the mesh weight can be approximately between 15 $g/cm^2$ to 35 $g/cm^2$ (e.g., 20 $g/cm^2$, 25 $g/cm^2$, 30 $g/cm^2$). In some embodiments, the mesh can be made, at least in part, of a synthetic material because the synthetic material can have a relatively high strength that can support a bodily portion (e.g., a urethra of a patient) without deforming (e.g., sagging, stretching) over time in an undesirable fashion compared with other materials.

The practitioner may install the sling 104 into the patient to lift or to provide support to the patient's urethra. In other embodiments, the sling 104 may be used to lift or provide support to another portion of the body of the patient, such as another tissue or organ. The practitioner may tension the sling 104 while the sling 104 is inside the patient so that the sling 104 remains in place and holds the patient's urethra in the appropriate location. For example, in some embodiments, the sling 104 is configured to help hold the patient's urethra in the appropriate location to allow the patient to control urine flow (or to avoid incontinence).

Handles 106A, 106B may be components of the implant assembly. The handles 106A, 106B may be made of rigid material, such as plastic, and may each be made of two planar materials, or of thin flattened tubes, according to example embodiments. The handles 106A, 106B may also be made of a strip of material of any preferred shape, such as a suture, a rope, a wire, mesh, or a continuation of the length of the sling 104. The handles 106A, 106B may be attached to opposite ends of the sling 104. The ends of the sling 104 may, for example, be inserted inside the handles 106A, 106B, and attached to the handles 106A, 106B, such as by heat sealing the sling 104 to the handles 106A, 106B. The ends and/or tangs of the sling 104 may be disposed within a cavity or otherwise covered by the handles 106A, 106B. The handles 106A, 106B may be coupled to the sling 104 by any known coupling means such as by heat tack, fastener, glue, or sewing.

The practitioner may use the handles 106A, 106B to guide the placement of the sling 104 inside the patient, and may cut the handles 106A, 106B off of the sling 104 after the sling 104 has been placed into the patient. The handles 106A, 106B may also give the practitioner additional length to place the sling 104 inside the patient. In some embodiments, the handles 106A, 106B may be formed of a different material than the sling 104. In some embodiments, the handles 106A, 106B may be formed of a material that is cheaper to produce or use than the material that is used to form the sling 104.

Elongated members 108A, 108B may be components of the implant assembly. The elongated members 108A, 108B may be made of rigid material, such as plastic, and may each be made of two planar materials, or may be tubular (and may be a flattened tube), in either example defining a lumen through which the handles 106A, 106B and sling 104 may pass. The elongated members 108A, 108B may each include slits or apertures extending from an outer portion of the elongated members 108A, 108B into the lumen. The handles 106A, 106B and sling 104 may be threaded into a first of the slits or apertures, through the lumen, and out of a second of the slits or apertures.

Dilators 110A, 110B may be components of the implant assembly. The dilators 110A, 110B may be made of a rigid material, such as plastic. The dilators 110A, 110B may be narrower at one end than at the opposite end, enabling the dilators to penetrate and dilate or expand the patient's tissue and guide the insertion and placement of the sling 104. In some embodiments, the dilators 110A, 110B may have a large length. For example, in some embodiments, the dilators 110A, 110B may be longer than the length of sling 104. In other embodiments, the dilators 110A, 110B may have a small length. For example, in some embodiments, the dilators 110A, 110B may be shorter than the length of the sling 104. The dilators 110A, 110B may be of any cross-sectional shape. For example, the dilators 110A, 110B may have a round or circle cross-sectional shape or may have a different cross-sectional shape, such as a rectangular, square, or oval cross-sectional shape.

The dilators 110A, 110B may each be attached to one of the handles 106A, 106B and/or elongated members 108A, 108B. The dilators 110A, 110B may each be heat sealed, for example, to the respective handle 106A, 106B and elongated member 108A, 108B.

A template 112 may be used by a manufacturer of the implant assembly to measure and facilitate the cutting of the elongated members 108A, 108B. The template 112 may, for example, be inserted into the lumens of the elongated members 108A, 108B, and guide cutting of the slits or apertures of the elongated members 108A, 108B, and may also guide trimming the tips and/or tails of the elongated members 108A, 108B.

While the illustrated embodiments show the implant assembly as a sling (for example having a body portion and two arms or extension portions), in some embodiments, the implant assembly includes a different shaped implant. In some embodiments, the implant may have more than two arms or extension portions that extend from a body portion. For example, the implant may have four, six, or more arms.

Figure 2:
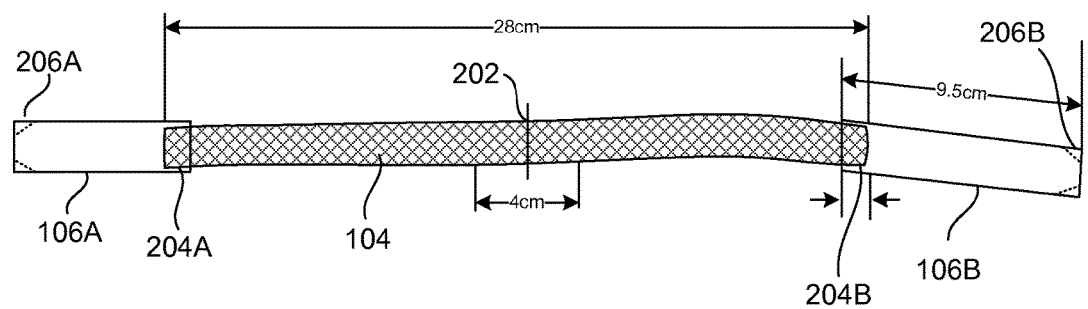
FIG. 2 illustrates a sling inserted into handles according to an example embodiment.

FIG. 2 is a diagram showing opposite ends of the sling 104 inserted into the handles 106A, 106B according to an example embodiment. In this example, the sling 104 may be twenty-eight centimeters long. However, the sling 104 may be other lengths, such as from twenty-six to thirty centimeters, twenty-four to thirty-two centimeters, or twenty to thirty-six centimeters, as non-limiting examples.

A center 202 of the sling 104 may be a portion in the middle of the sling where a tab (not shown in FIG. 2) may be attached. The tab may be used to guide the placement of the sling 104 inside the patient. In the example shown in FIG. 2, the central portion is four centimeters long, with a mid-point at the center 202 of the sling 104. However, the central portion may be other lengths, such as between three and five centimeters, two and six centimeters, or between one and seven centimeters, according to example embodiments.

Opposite end portions 204A, 204B of the sling 104 may be inserted into the handles 106A, 106B. The end portions 204A, 204B may be attached or coupled inside the handles 106A, 106B, such as by heat sealing or gluing the end portions 204A, 204B inside the handles 106A, 106B.

Either before or after the end portions 204A, 204B of the sling 104 are inserted into the handles 106A, 106B, tips 206A, 206B of the handles 106A, 106B may be trimmed. The tips 206A, 206B may be on opposite ends of the handles 106A, 106B from the ends into which the end portions 204A, 204B of the sling 104 were inserted. The tips 206A, 206B may be trimmed at angles to remove the corners, facilitating the passage of the handles 106A, 106B into the respective lumens of the elongated members 108A, 108B (shown in FIG. 1). The dashed lines in FIG. 2 show lines along which the tips 206A, 206B of the handles 106A, 106B may be trimmed.

Figure 3:
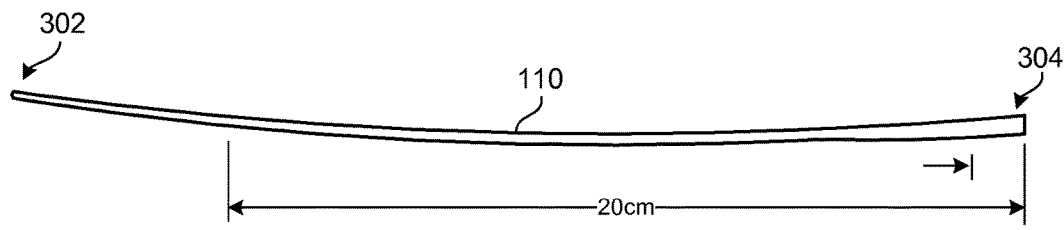
FIG. 3 illustrates a dilator according to an example embodiment.

FIG. 3 is a diagram of a dilator 110 according to an example embodiment. The dilator 110 shown in FIG. 3 may be representative of either of the dilators 110A, 110B shown in FIG. 1. The dilator 110 may include a narrow end 302, which will penetrate the patient's tissue, and a broad end 304, which will be attached to the respective handle 106A, 106B (shown in FIGS. 1 and 2) and/or elongated member 108A, 108B (shown in FIG. 1). The broad end 304 of the dilator 110 may be attached to the handle 106A, 106B and/or elongated member 108A, 108B by inserting the broad end 304 into the lumen or recess of the handle 106A, 106B and/or elongated member and then heat sealed or glued. In the example shown in FIG. 3, 1.5 centimeters of the broad end 304 may be inserted into the handle 106A, 106B and/or elongated member 108A, 108B. However, other lengths of the broad end 304, such as between one and two centimeters, or between 0.5 and 2.5 centimeters, may be inserted into and attached to the handle 106A, 106B and/or elongated member 108A, 108B.

The dilator 110 may be cut to an appropriate or desired length. In some embodiments, the manufacture may provide implant assemblies with varying dilator lengths to accommodate different sized patients. In such embodiments, the medical practitioner may select, from a group of sling assemblies, each with different dilator lengths, which implant assembly to use for a specific patient. In the example shown in FIG. 3, the determined length is twenty centimeters. However, the appropriate length may be determined to be other lengths, depending on the patient's size and anatomy.

Figure 4:
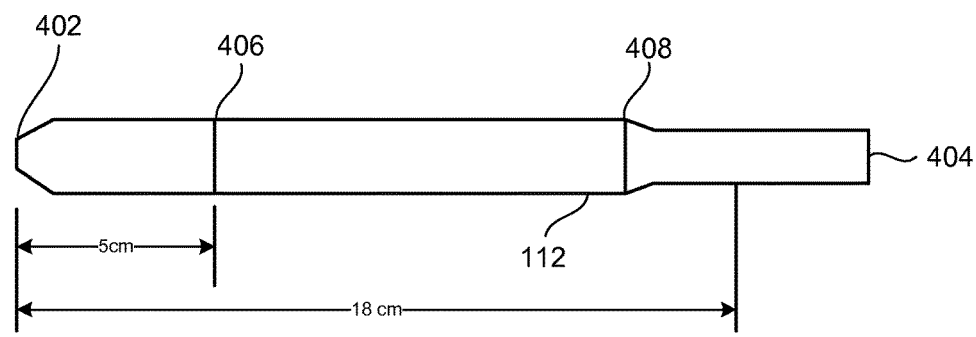
FIG. 4 illustrates a template for cutting an elongated member according to an example embodiment.

FIG. 4 is a diagram of a template 112 for cutting an elongated member 108A, 108B (shown in FIG. 1) according to an example embodiment. The manufacturer may use the template 112 when manufacturing or assembling the implant assembly. The template 112 may include a tip portion 402 at a first end. The tip portion 402 may be wedge-shaped, or narrower at the end, facilitating entry of the tip portion 402 into an elongated member 108A, 108B. The template 112 may also include a narrower tail portion 404 at an opposite end from the tip portion 402. With the template 112 inside the elongated member 108A, 108B, the manufacturer or assembler of the implant assembly may cut away a portion of the tubing, or one or both of the planar materials, of the elongated member 108A, 108B, which surrounds both the tip portion 402 and the tail portion 404 of the template 112. Cutting away the portion of the tubing or one of the planar materials may leave the lumen of the elongated member 108A, 108B exposed at opposite ends.

The template 112 may also include slit markings 406, 408. In an example embodiment, the slit markings 406, 408 may be ten centimeters away from each other. The slit marking 406 may be five centimeters from an end of the tip portion 402. The template 112 may be inserted eighteen centimeters inside the elongated member 108A, 108B. With the template 112 inside the elongated member 108A, 108B, the elongated member 108A, 108B may be cut from outside the elongated member 108A, 108B into the lumen along the lines demarcated by the slit markings 406, 408. The cutting along these lines may form slits or apertures in the elongated members 108A, 108B through which the handles 106A, 106B and sling 104 may be threaded or inserted.

Figure 5:
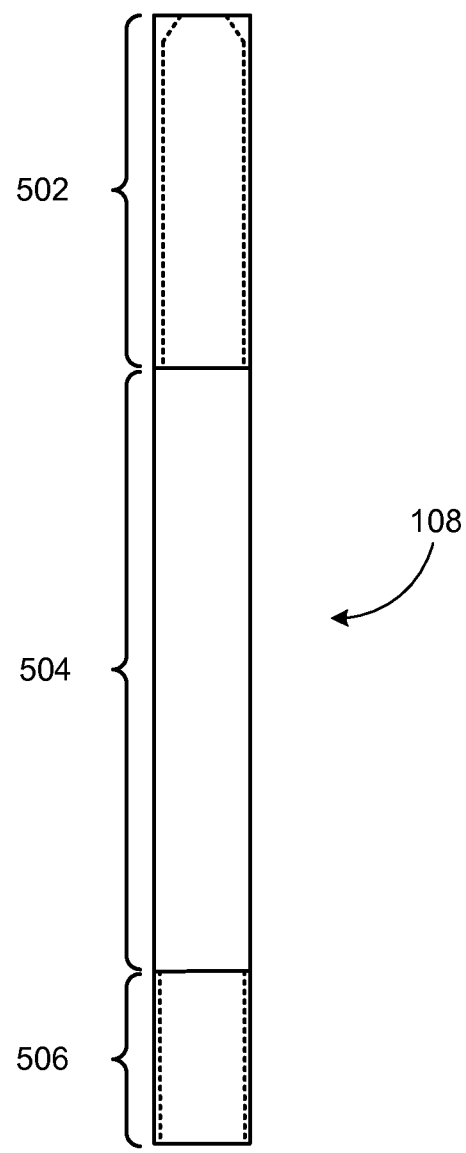
FIG. 5 illustrates the elongated member according to an example embodiment.

FIG. 5 is a diagram of one of the elongated members 108A, 108B (referred to non-specifically as elongated member 108) according to an example embodiment. The elongated member 108 may be made of a rigid material, such as plastic. The elongated member 108 may be made of two planar members sealed or otherwise attached at the edges to form a lumen extending lengthwise (between the top and bottom of the page as shown in FIG. 5) between the two planar members, or may be made of a thin flat tubular member defining a lumen extending along the length of the elongated member 108A, 108B.

As discussed above with respect to FIG. 4, the template 112 (shown in FIG. 4) may have been inserted into the elongated member 108 to guide cutting away portions of the elongated member 108. In a tip portion 502 of the elongated member 108, a cut along both sides of the elongated member 108 along the dashed lines is made to narrow the elongated member 108 and expose the lumen. A center portion 504 of the elongated member 108 may be left intact so that the elongated member continues to define the lumen. In a tail portion 506 of the elongated member 108, the manufacturer or assembler of the implant assembly may cut one side (a "top" side) of the elongated member 108 off, removing the top side or layer. The manufacturer or assembler may also cut portions of the sides of the tail 506 of the elongated member 108 off, as shown by the dashed lines in FIG. 5.

Figure 6:
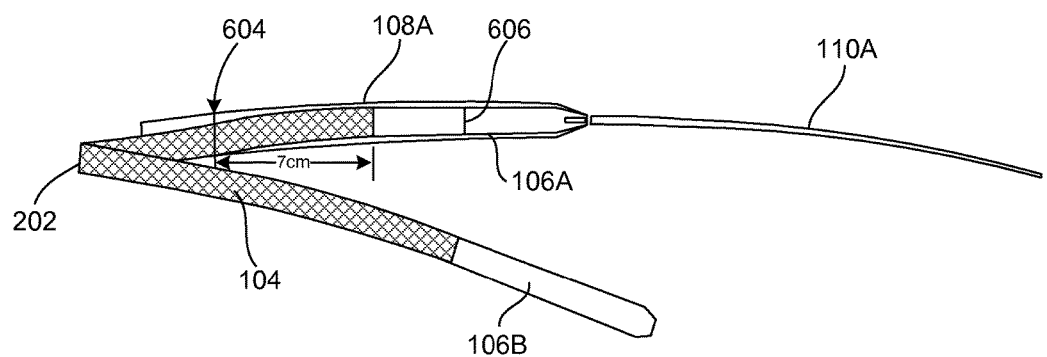
FIG. 6 illustrates an assembly according to an example embodiment.

FIG. 6 is a diagram showing assembly of the implant assembly according to an example embodiment. The assembly shown in FIG. 6 may be performed by the manufacture of the implant assembly. The handle 106A, after being attached to the end portion 204A (referenced in FIG. 2) of the sling 104, is threaded through the slit or aperture 604 of the elongated member 108A, pulling the sling 104 with the handle 106A into the lumen of the elongated member 108A. The handle 106A is then threaded through the slit or aperture 606 of the elongated member 108A, so that the handle 106A is partly inside the lumen (defined by the center portion 504 shown in FIG. 5) of the elongated member 108 and partly outside the lumen and resting along the tip portion 502 (shown in FIG. 5) of the elongated member 108A. More than half of the sling 104 may be inside of the lumens of the two elongated members 108A, 108B, or less than half of the sling 104 may be inside of the lumens of the two elongated members 108A, 108B, according to example embodiments. In another embodiment, the handle 106A may be threaded thought the slits or apertures of the elongated member 108A such that the handle 106A is disposed outside of the lumen defined by the elongated member 108A between the slits or apertures and is disposed within the lumen between each end and the adjacent slit or aperture.

The practitioner may align a tip or end of the handle 106A with a tip or end of the elongated member 108A. After the tips or ends of the handle 106A and elongated member 108A are aligned, the dilator 110A may be attached to the tip or end of the handle 106A and/or elongated member 108A. The dilator 110A may be attached to the tip or end of the handle 106A and/or elongated member 108A by, for example, heat bonding. The elongated member 108B (shown in FIG. 1) and dilator 110B (shown in FIG. 1) may be attached to the handle 106B in a similar manner to the attachment of the elongated member 108A and dilator 110A to the handle 106A.

Figure 7:
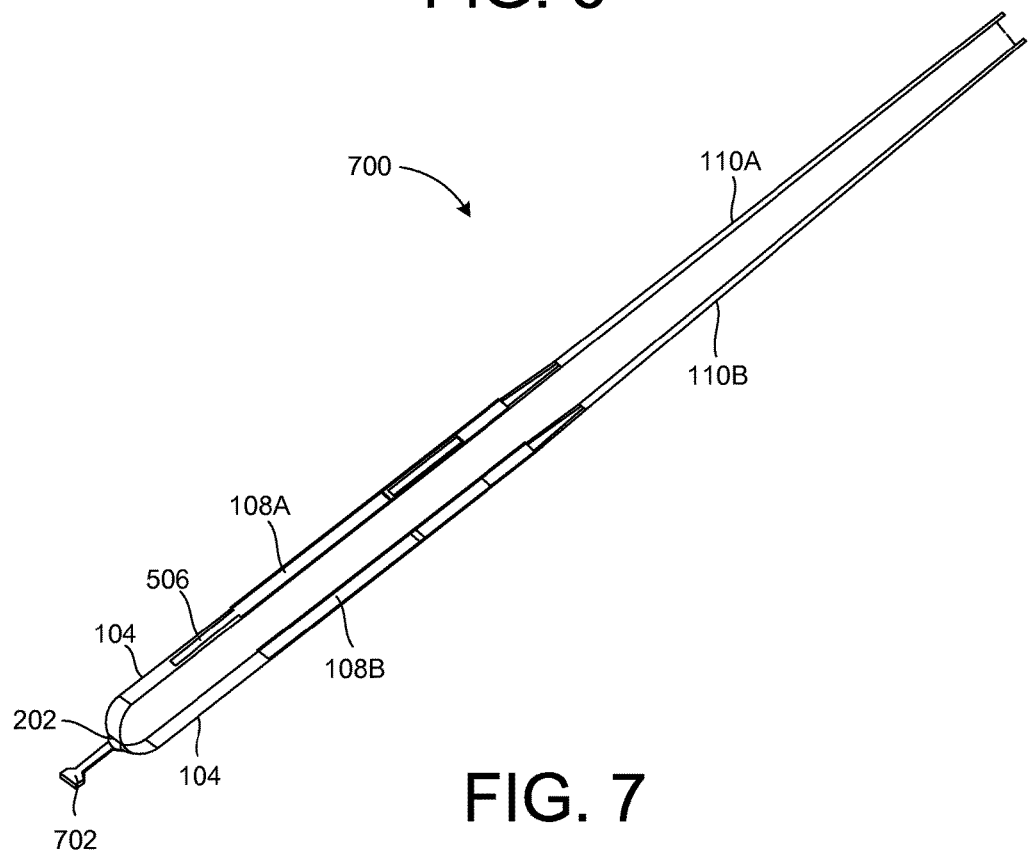
FIG. 7 illustrates the implant assembly according to an example embodiment.

FIG. 7 is a diagram of the implant assembly 700 according to an example embodiment. While the handles 106A, 106B are not visible in FIG. 7, FIG. 7 shows the sling 104 extending out of the elongated members 108A, 108B. FIG. 7 also shows the dilators 110A, 110B extending from the elongated members 108A, 108B. FIG. 7 also shows the narrowed tail portion 506 of the elongated member 108A formed by cutting the sides out of the tail portion 506 based on the markings of the template 112 (shown in FIGS. 1 and 4). FIG. 7 also shows a tab 702 extending from the center 202 of the sling 104 (i.e., outside the U-shaped enclosure formed by the curve of the sling 104). The tab 702 may be positioned on an outer surface of the sling 104, enabling the practitioner to place the sling 104 against the urethra and adjust the elongated members 108A, 108B.

Figure 8:
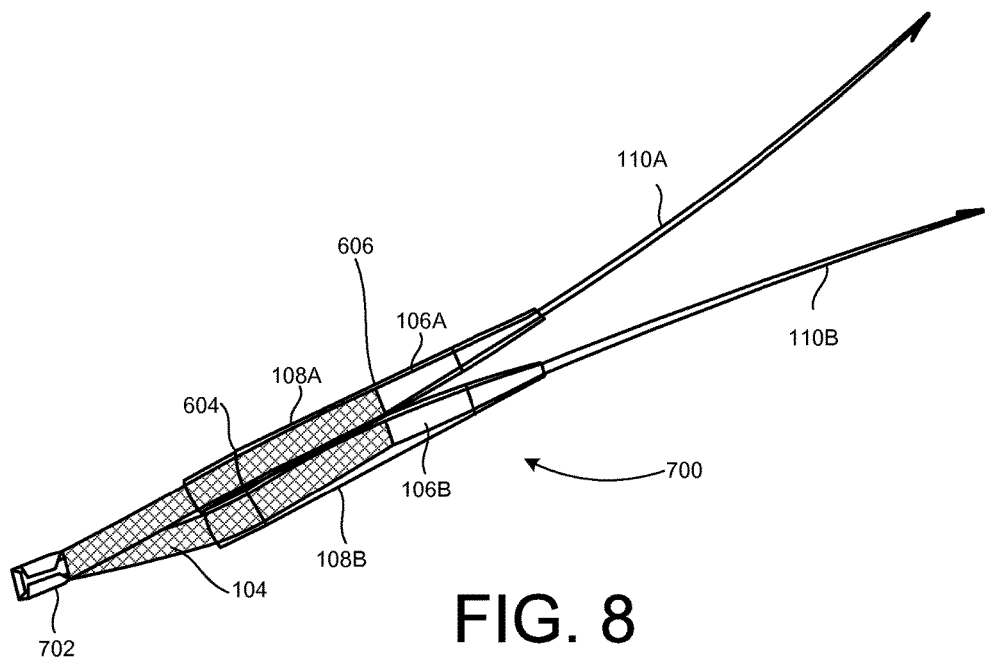
FIG. 8 illustrates the implant assembly according to another example embodiment.

FIG. 8 is a diagram of the implant assembly 700 according to another example embodiment. FIG. 8 also shows the tab 702 extending from the sling 104. FIG. 8 shows the handle 106A and sling 104 threaded into the lumen of the elongated member 108A through the aperture 604, and out of the lumen through the aperture 606. The handle 106B and sling 104 may also be threaded into and out of a lumen of the elongated member 108B through corresponding apertures in the elongated member 108B. Dilators 110A, 110B may be attached to the elongated members 108A, 108B and/or handles 106A, 106B, as discussed above with respect to FIG. 6.

Figure 9:
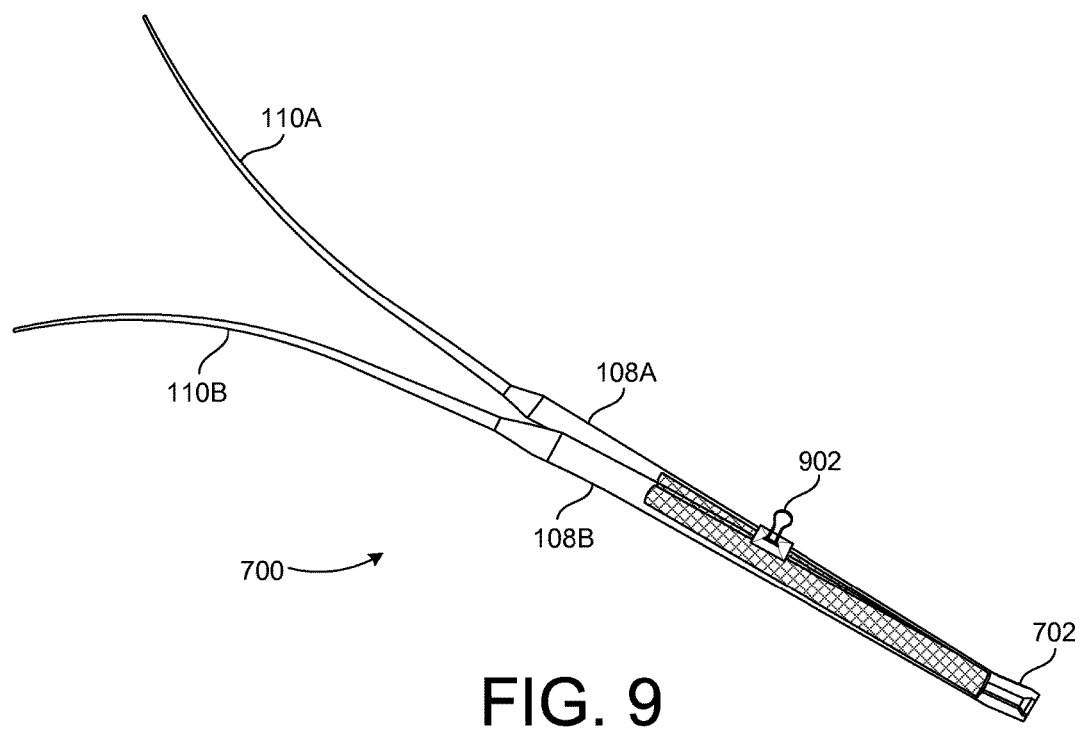
FIG. 9 illustrates the implant assembly according to another example embodiment.

FIG. 9 is a diagram of the implant assembly 700 according to another example embodiment. In this example, as in the examples shown and described with respect to FIGS. 7 and 8, the tab 702 extends from the sling 104; the handles 106A, 106B (not shown in FIG. 9) and sling 104 extend through the respective lumens of the elongated members 108A, 108B; and the dilators 110A, 110B are attached to the handles 106A, 106B and/or elongated members 108A, 108B. In this example, a clip 902 or clip member squeezes and/or holds the two elongated members 108A, 108B or other portions of the implant assembly 700 together. In some embodiments, the clip 902 may prevent the implant assembly 700 from tangling and/or dangling in undesired locations or directions such as below an operating table.

Figure 10:
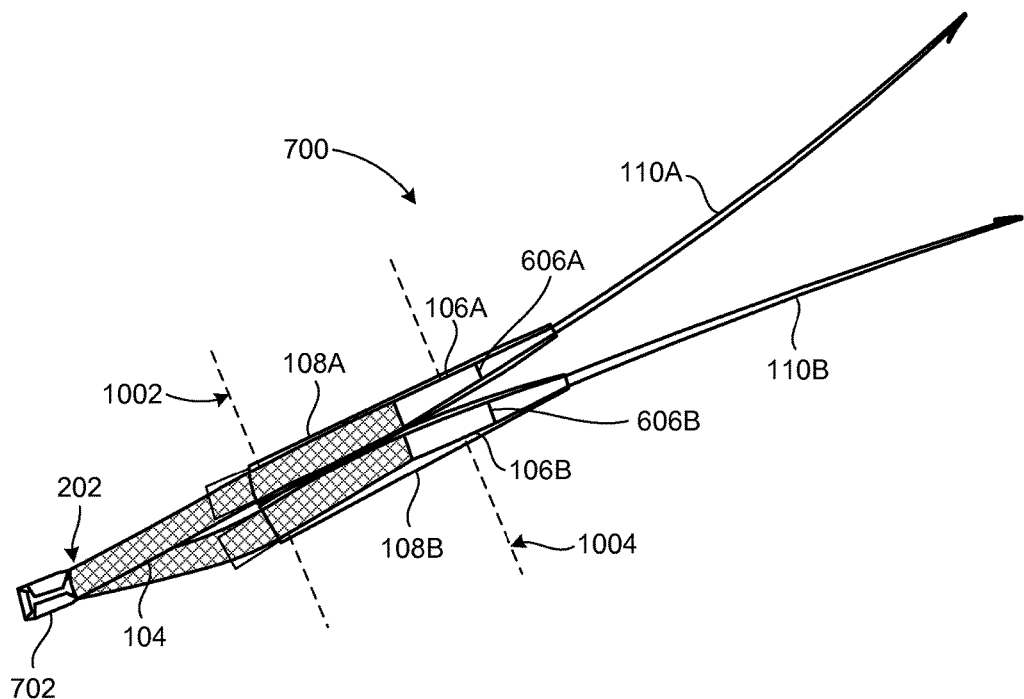
FIG. 10 illustrates the implant assembly schematically inserted relative to a vaginal incision and skin level of a patient according to an example embodiment.

FIG. 10 is a diagram showing where the implant assembly 700 is inserted relative to a vaginal incision 1002 and skin level 1004 of a patient according to an example embodiment. A practitioner may have made a vaginal incision in an upper wall of the patient's vagina at the point shown by the dashed lines of the vaginal incision level 1002. The practitioner may push the implant assembly 700, leading with the dilators 110A, 110B, through the patient's upper pelvic region. The dilators 110A, 110B may penetrate the skin of the patient's upper pelvic region and extend out of the patient's body.

The practitioner may position the implant assembly 700 so that the dilators 110A, 110B are outside the patient's body, and the handles 106A, 106B and tip portions 502 (not referenced in FIG. 10) of the elongated members 108A, 108B are partially extending out of the patient's pelvic region. As shown in FIG. 10, apertures 606A, 606B (corresponding to aperture 606 described above with respect to FIGS. 6 and 8) may be above the patient's skin level 1004 and/or outside the patient's body, and the sling 104 may be fully inside the patient's body. The portion of the sling 104 that is inside the lumen of the elongated members 108A, 108B, and the elongated members 108A, 108B, may be on both sides of the vaginal incision level 1002. The portion of the sling 104 that is not inside the elongated members 108A, 108B and the tab 702 may be below the vaginal incision level 1002 and inside the patient's vagina.

Figure 11:
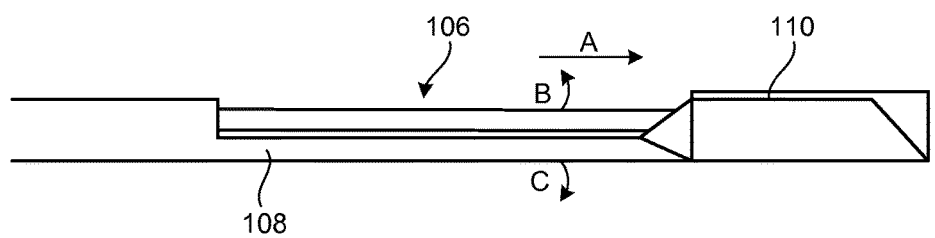
FIG. 11 illustrates the elongated member, handle, or both, according to an example embodiment.

FIG. 11 is a diagram showing where a practitioner cuts through the elongated member 108, handle 106 (which may correspond to either of the handles 106A, 106B), or both, according to an example embodiment. After positioning the implant assembly 700 as shown and described with respect to FIG. 10, the practitioner may cut in a direction of arrow A through the elongated member 108, the handle 106, or both, at a point just behind the dilator 110. After cutting, the practitioner may separate the elongated member 108 and/or handle 106 by pulling on the two halves in opposite directions, denoted by arrows B and C. The practitioner may thereafter remove the elongated member 108 and/or handle 106 from the patient's body.

Figure 12:
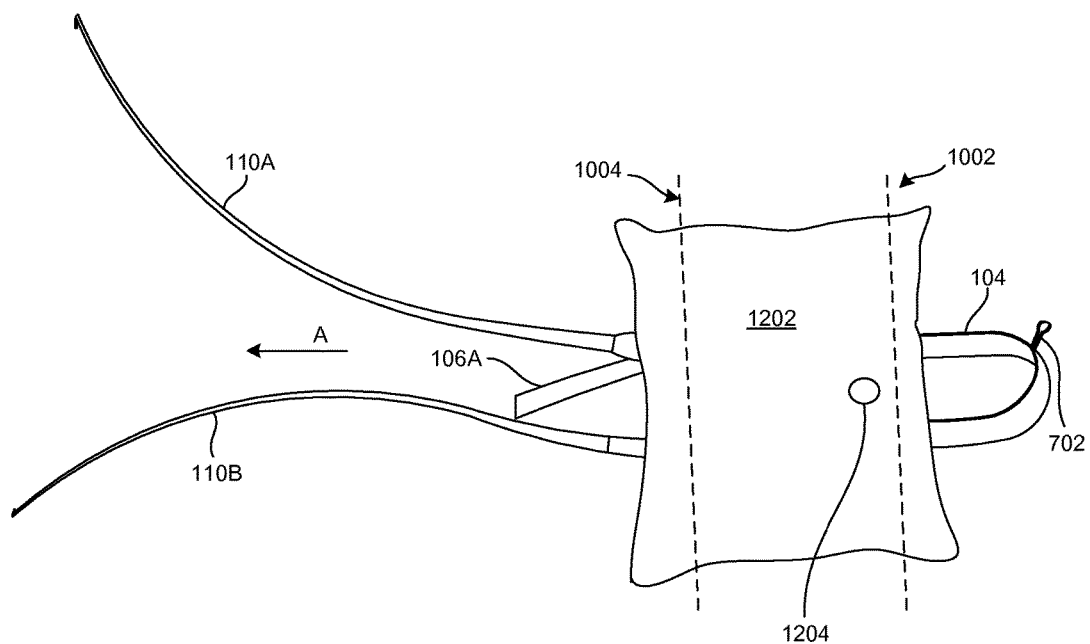
FIG. 12 illustrates the sling according to an example embodiment.

FIG. 12 is a diagram showing a direction in which the sling 104 is pulled to narrow a space between the sling 104 and a urethra 1204 of the patient according to an example embodiment. In FIG. 12, the location of the implant assembly 700 with respect to the vaginal incision level 1002 and skin level 1004 may be similar to the location shown and described with respect to FIG. 10. The implant assembly 700 may extend through the vaginal incision 1002, the patient's upper pelvic tissue 1202, and the skin level 1004 through which the implant assembly extends out of the patient's body. The practitioner may pull on the handles 106 in the direction denoted by arrow A (which was also shown in FIG. 11), thereby narrowing the space between the urethra 1204 and the sling 104. The practitioner may increase the space between the urethra 1204 and the sling 104 by pulling on the tab 702 and/or the portion of the sling 104 that extends below (or to the right of, from the perspective of FIG. 12) the vaginal incision level 1002 in an opposite direction of arrow A. The practitioner may also center the central portion of the sling 104 by moving the tab 702.

After the practitioner has positioned the sling 104, the elongated members 108A, 108B (not shown in FIG. 12) have been cut as shown and described with respect to FIG. 11, and the dilators 110A, 110B have been removed, the practitioner can remove the elongated members 108A, 108B by grasping the elongated members 108A, 108B and pulling the elongated members 108A, 108B away from the patient's body in the direction of arrow A. The practitioner may then trim the ends of the sling 104 to skin level 1004. The practitioner may remove the tab 702 by cutting an attachment point, such as a leader, and pulling the tab 702 in the opposite direction of arrow A.

Figure 13:
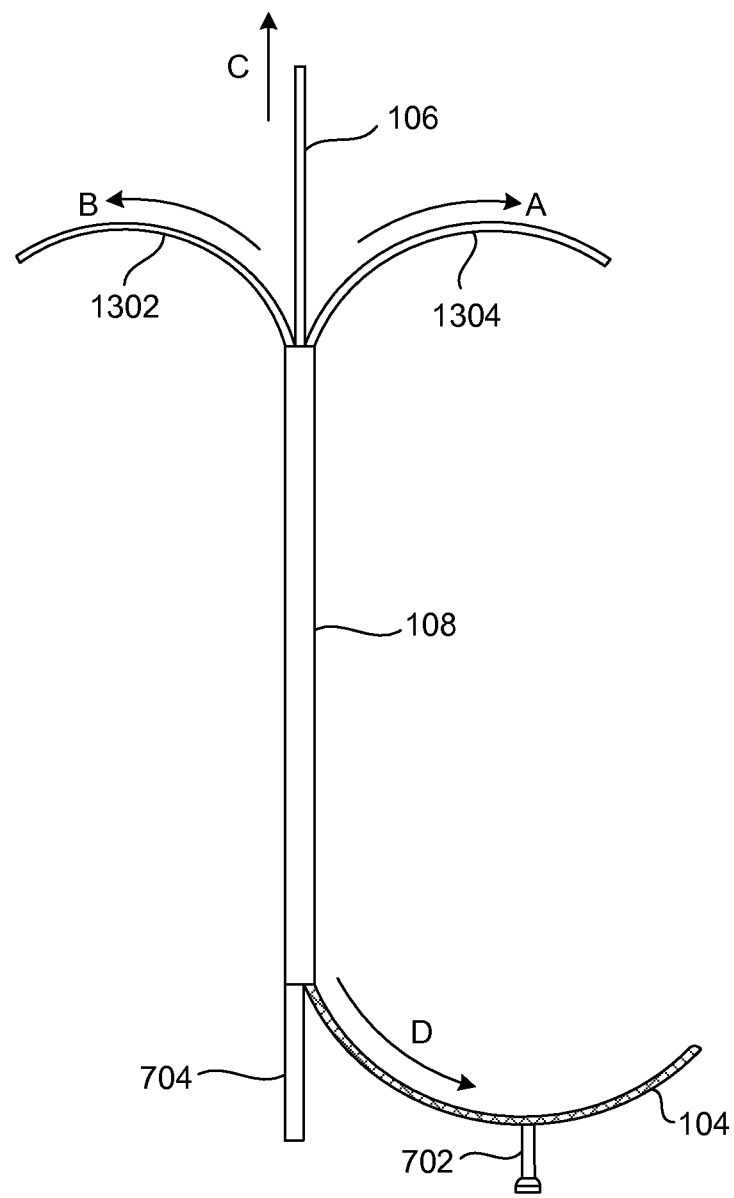
FIG. 13 illustrates layers of the elongated member according to an example embodiment.

FIG. 13 is a diagram showing layers 1302, 1304 (in some embodiments, the layers may be planar in shape) of the elongated member 108 being peeled or torn away from the sling 104 and handle 106 according to an example embodiment. The elongated member 108 may have been cut as described with respect to FIG. 11. The cutting of the elongated member 108 may cause the elongated member 108 to form two layers 1302, 1304. The practitioner may peel the two layers 1302, 1304 away from the handle 106 and sling 104 in the directions shown by arrows A and B. The practitioner may then remove the handle 106 by pulling the handle 106 in the direction of arrow C, and may adjust the sling's 104 position within the patient by pulling in the directions of either arrow C or D.

Figure 14:
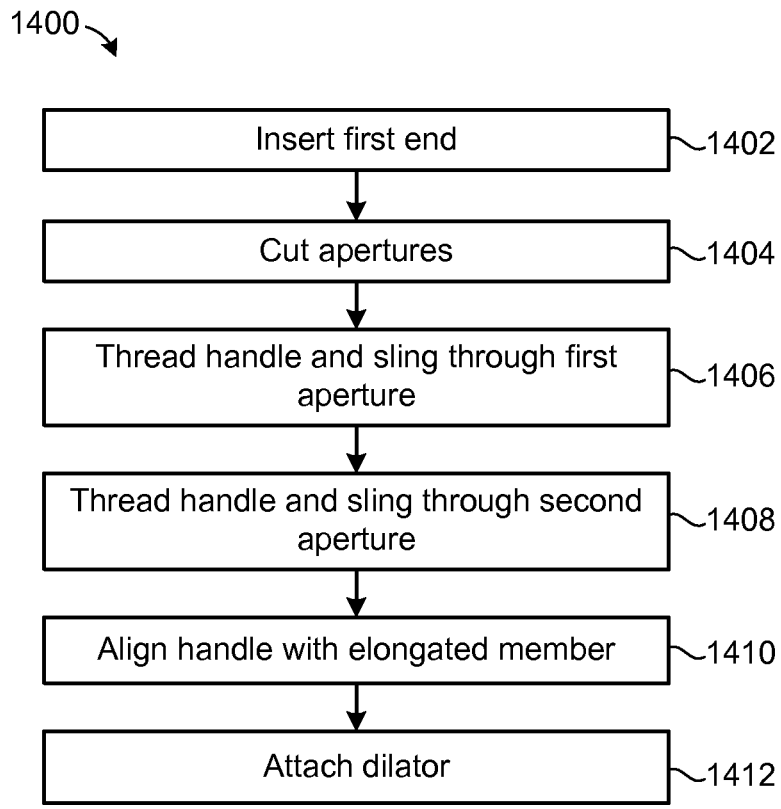
FIG. 14 is a flowchart showing a method of assembling an implant for incontinence repair according to an example embodiment.

FIG. 14 is a flowchart showing a method 1400 of assembling an implant for incontinence repair according to an example embodiment. The method 1400 may be performed by a manufacture of the implant assembly. According to an example embodiment, the method may include inserting an end of an incontinence sling into a first end of a handle (1402). The method 1400 may also include cutting at least a first aperture and a second aperture into an elongated member, the elongated member defining a lumen, each of the first and second apertures extending from outside the elongated member into the lumen (1404). The method 1400 may also include threading the handle and the incontinence sling through the first aperture from outside the elongated member into the lumen (1406). The method 1400 may also include threading the handle and incontinence sling through the second aperture from inside the lumen to outside the elongated member (1408). The method 1400 may also include aligning a second end of the handle with an end of the elongated member, the second end of the handle being opposite from the first end of the handle (1410). The method 1400 may also include attaching a dilator to the second end of the handle (1412).

According to an example embodiment, the elongated member may cover more than half of the incontinence sling after the first handle and incontinence sling are threaded through the first and second apertures of the elongated member.

According to an example embodiment, the elongated member may cover less than half of the incontinence sling after the handle and incontinence sling are threaded through the first and second apertures of the elongated member.

According to an example embodiment, the attaching the dilator may include heat bonding the dilator to the end of the handle that is aligned with the end of the elongated member.

According to an example embodiment, the method 1400 may further include heat sealing the first end of the incontinence sling to the handle after inserting the first end of the incontinence sling into the first end of the handle.

According to an example embodiment, the method 1400 may further include trimming at least one corner on the second end of the handle.

According to an example embodiment, the method 1400 may further include trimming two corners on the second end of the handle.

According to an example embodiment, the method 1400 may further include inserting a template into the lumen of the elongated member, the template including markings to guide the cutting the at least the first aperture and the second aperture. The cutting may include cutting the at least the first aperture and the second aperture into the elongated member based on the markings of the template while the template is inside the lumen of the elongated member.

According to an example embodiment, the method 1400 may further include determining an appropriate length of the dilator based on anatomical dimensions of a patient, and cutting the dilator to the determined appropriate length.

According to an example embodiment, the method 1400 may further include squeezing or coupling the first elongated member to a second elongated member with a clip.

Figure 15:
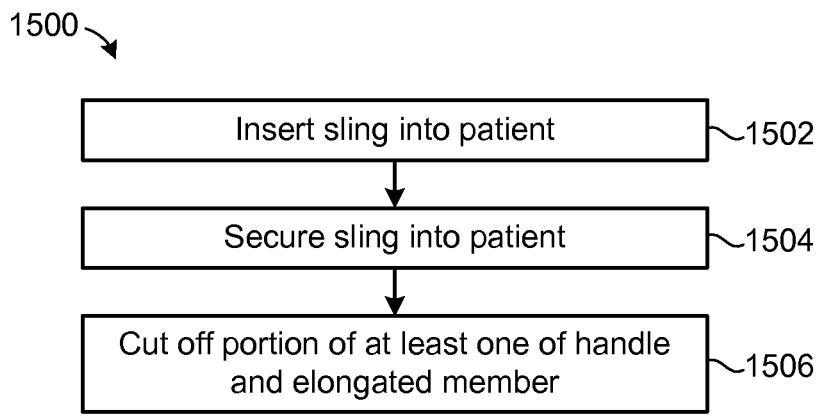
FIG. 15 is a flowchart showing a method of inserting a sling into a patient to treat incontinence according to an example embodiment.

FIG. 15 is a flowchart showing a method 1500 of inserting a sling into a patient to treat incontinence according to an example embodiment. The method 1500 may include inserting the sling into the patient through a vaginal incision (such as an anterior vaginal incision) in the patient, at least one end of the sling being attached to a handle, a portion of the sling extending through a lumen of an elongated member (1502). The method 1500 may also include securing the sling inside the patient with a portion of the elongated member extending out of the vaginal incision into the patient's vagina (1504). The method 1500 may also include cutting off at least a portion of at least one of the handle and the elongated member from the sling after securing the sling inside the patient (1506).

According to an example embodiment, the elongated member may include a first aperture and a second aperture, the sling extending through the first aperture, into the lumen, and out of the lumen through the second aperture. The inserting the sling into the patient may include inserting the sling through a vaginal incision using a dilator connected to an end of the elongated member which is opposite from the portion of the elongated member extending out of the incision into the patient's vagina so that the dilator and opposite end of the elongated member are outside the patient's body. The method 1500 may further include cutting the opposite end and the dilator off of the elongated member.

According to an example embodiment, the method 1500 may further include tensioning the sling by pulling on the sling while the sling is inside the lumen of the elongated member and the sling and elongated member are inside the patient.

According to an example embodiment, the elongated member may remain stationary relative to the patient while the sling is tensioned.

According to an example embodiment, the method 1500 may further include removing the elongated member from the patient after tensioning the sling.

In some embodiments, an implant assembly includes a first handle; a first elongated member defining a plurality of apertures and defining a first lumen; and a support member extending through the first lumen of the first elongated member. The support member includes a first end and a second end. The first end being configured to be coupled to the first handle.

In some embodiments, the implant assembly includes a second handle; and a second elongated member defining a second lumen. The support member extends through the second lumen of the second elongated member and the second end of the support member is attached to the second handle. In some embodiments, the implant assembly includes a dilator attached to an end of the first handle that is opposite from the first end of the support member.

In some embodiments, a method of inserting a sling into a patient to treat incontinence includes inserting the sling into the patient through a vaginal incision in the patient, at least one end of the sling being attached to a handle, a portion of the sling extending through a lumen of an elongated member; extending the handle through the patient's body and pushing the handle through the skin from the inside out; securing the sling inside the patient with a portion of the elongated member extending out of the vaginal incision into the patient's vagina; and cutting off at least a portion of at least one of the handle extending outside the body of the patient and the elongated member from the sling after securing the sling inside the patient.

In some embodiments, the elongated member includes a first aperture and a second aperture, the sling extending through the first aperture, into the lumen, and out of the lumen through the second aperture and the inserting the support member into the patient includes penetrating a pelvic wall of the patient with a dilator connected to an end of the elongated member which is opposite from the portion of the elongated member extending out of the incision into the patient's vagina so that the dilator and opposite end of the elongated member are outside the patient's body. In some embodiments, the method includes cutting the opposite end and the dilator off of the elongated member.

In some embodiments, the method includes tensioning the support member by pulling on the support member while the support member is inside the lumen of the elongated member and the sling and elongated member are inside the patient. In some embodiments, the elongated member remains stationary relative to the patient while the sling is tensioned.

In some embodiments, the method includes removing the elongated member from the patient after tensioning the sling.

In some embodiments, a method of assembling an implant includes inserting an end of a support member into a first end of a handle; cutting at least a first aperture and a second aperture into an elongated member, the elongated member defining a lumen, each of the first and second apertures extending from outside the elongated member into the lumen; threading the handle and the support member through the first aperture from outside the elongated member into the lumen; threading the handle and support member through the second aperture from inside the lumen to outside the elongated member; aligning a second end of the handle with an end of the elongated member, the second end of the handle being opposite from the first end of the handle; and attaching a dilator to the second end of the handle.

In some embodiments, the elongated member covers more than half of the support member after the first handle and support member are threaded through the first and second apertures of the elongated member.

In some embodiments, the elongated member covers less than half of the support member after the handle and the support member are threaded through the first and second apertures of the elongated member. In some embodiments, the attaching the dilator includes heat bonding the dilator to the end of the handle that is aligned with the end of the elongated member. In some embodiments, the method includes heat sealing the first end of the support member to the handle after inserting the first end of the incontinence sling into the first end of the handle. In some embodiments, the method includes trimming at least one corner on the second end of the handle. In some embodiments, the method includes trimming two corners on the second end of the handle.

In some embodiments, the method includes inserting a template into the lumen of the elongated member. The template includes markings to guide the cutting the at least the first aperture and the second aperture. In some embodiments, the cutting includes cutting the at least the first aperture and the second aperture into the elongated member based on the markings of the template while the template is inside the lumen of the elongated member. In some embodiments, the method includes determining an appropriate length of the dilator based on anatomical dimensions of a patient; and cutting the dilator to the determined appropriate length. In some embodiments, the method includes coupling the elongated member to a second elongated member with a clip.

While certain features of the described implementations have been illustrated as described herein, many modifications, substitutions, changes and equivalents will now occur to those skilled in the art. It is, therefore, to be understood that the appended claims are intended to cover all such modifications and changes as fall within the true spirit of the embodiments of the invention.

What is claimed is:

1. An implant assembly comprising:
an implant having a first material, the implant having a central portion, a first end portion, and a second end portion;
a handle having a second material, the handle configured to be coupled to the first end portion of the implant, the second material being different than the first material;
an elongated member defining a tapered tip portion, a central region, and a tail portion, the elongated member defining a first slit between the tapered tip portion and the central region, and a second slit between the central region and the tail portion, the elongated member defining a lumen between the first slit and the second slit, the implant configured to be at least partially disposed within the lumen of the elongated member, the tapered tip portion having a first lateral side and a second lateral side, the tapered tip portion having a third slit along the first lateral side, and a fourth slit along the second lateral side, the handle including a first portion disposed within the lumen between the first slit and the second slit, and a second portion disposed outside the lumen; and
a dilator coupled to at least one of the handle and the elongated member.

2. The implant assembly of claim 1, wherein the first material is a mesh material, and the second material is a plastic material.

3. The implant assembly of claim 1, wherein the implant has a first surface and a second surface opposite to the first surface, the second surface being separated from the first surface by a thickness of the implant, the tail portion covering a portion of the first surface of the implant but not the second surface of the implant.

4. The implant assembly of claim 1, wherein the tail portion has a width smaller than a width of the central region, the tapered tip portion having a width smaller than the width of the central region.

5. The implant assembly of claim 1, wherein the implant has a first surface and a second surface, the second surface being opposite to the first surface, wherein a distance between the first surface and the second surface defines a thickness of the implant, the tail portion configured to contact the first surface but not the second surface.

6. The implant assembly of claim 1, wherein the third slit and the fourth slit are disposed perpendicular to a portion of the first slit and a portion of the second slit.

7. The implant assembly of claim 1, wherein the handle defines a cavity, and the first end portion of the implant is inserted into the cavity of the handle.

8. The implant assembly of claim 7, wherein the first end portion of the implant includes tangs, and the tangs are disposed within the cavity of the handle.

9. The implant assembly of claim 1, wherein an end of the handle is aligned with an end of the elongated member.

10. The implant assembly of claim 1, wherein the dilator is coupled to the handle.

11. The implant assembly of claim 1, wherein the dilator is coupled to the elongated member.

12. The implant assembly of claim 1, wherein the handle is a first handle, the elongated member is a first elongated member, the lumen is a first lumen, and the dilator is a first dilator, the implant assembly further comprising:
a second handle having the second material, the second handle configured to be coupled to the second end portion of the implant;

a second elongated member defining a second lumen, the implant configured to be at least partially disposed within the second lumen of the second elongated member; and a second dilator coupled to at least one of the second handle and the second elongated member.

13. The implant assembly of claim 1, further comprising:

a tab coupled to the central portion of the implant.

14. An implant assembly comprising:

an implant having a first material, the implant having a first end portion and a second end portion;

a handle having a second material, the handle configured to be coupled to the first end portion of the implant, the second material being different than the first material;

an elongated member defining a lumen, the elongated member having a first end portion and a second end portion;

a template configured to be inserted into the elongated member, the template being a guide for cutting the first end portion of the elongated member and the second end portion of the elongated member, the template including a tip portion, a central region, and a tail portion, the template including a first slit marking disposed between the tip portion and the central region, and a second slit marking disposed between the tail portion and the central region; and a dilator configured to be coupled to at least one of the handle and the elongated member.

15. The implant assembly of claim 14, wherein the handle is a first handle, the elongated member is a first elongated member, the lumen is a first lumen, and the dilator is a first dilator, the implant assembly further comprising:

a second handle having the second material, the second handle configured to be coupled to the second end portion of the implant;

a second elongated member defining a second lumen, the implant configured to be at least partially disposed within the second lumen of the second elongated member; and a second dilator coupled to at least one of the second handle and the second elongated member.

16. The implant assembly of claim 14, wherein the tip portion has a wedged-shaped portion, the tail portion having a width smaller than a width of the central region.

\* \* \* \* \*